United States Patent
Ramani et al.

(10) Patent No.: US 11,353,411 B2
(45) Date of Patent: Jun. 7, 2022

(54) METHODS AND SYSTEMS FOR MULTI-MATERIAL DECOMPOSITION

(71) Applicant: GE Precision Healthcare LLC, Milwaukee, WI (US)

(72) Inventors: Sathish Ramani, Niskayuna, NY (US); Mingye Wu, Clifton Park, NY (US); Bruno De Man, Clifton Park, NY (US); Peter Edic, Albany, NY (US)

(73) Assignee: GE Precision Healthcare LLC, Milwaukee, WI (US)

( * ) Notice: Subject to any disclaimer, the term of this patent is extended or adjusted under 35 U.S.C. 154(b) by 200 days.

(21) Appl. No.: 16/889,699

(22) Filed: Jun. 1, 2020

(65) Prior Publication Data

US 2021/0372951 A1 Dec. 2, 2021

(51) Int. Cl.
*G06T 11/00* (2006.01)
*G01N 23/046* (2018.01)
*A61B 6/03* (2006.01)
*G06T 7/00* (2017.01)

(52) U.S. Cl.
CPC .......... *G01N 23/046* (2013.01); *G06T 11/005* (2013.01); *G06T 11/008* (2013.01); *A61B 6/032* (2013.01); *G06T 7/0012* (2013.01); *G06T 2207/30004* (2013.01); *G06T 2211/408* (2013.01)

(58) Field of Classification Search
CPC ... G01N 23/046; G06T 11/005; G06T 11/008; G06T 7/0012; G06T 2207/30004; G06T 2211/408; G06T 11/003; A61B 6/032
See application file for complete search history.

(56) References Cited

U.S. PATENT DOCUMENTS

| | | | |
|---|---|---|---|
| 6,674,835 B2 | 1/2004 | Kaufhold | |
| 9,977,140 B2 | 5/2018 | Wang | |
| 2008/0187091 A1* | 8/2008 | Basu | G01N 23/046 382/131 |
| 2013/0343624 A1* | 12/2013 | Thibault | G06T 11/006 382/131 |

OTHER PUBLICATIONS

EP application 21173966.9 filed May 14, 2021—extended Search Report dated Nov. 9, 2021; 11 pages.

(Continued)

*Primary Examiner* — Courtney D Thomas
(74) *Attorney, Agent, or Firm* — McCoy Russell LLP

(57) ABSTRACT

Various methods and systems are provided for multi-material decomposition for computed tomography. In one embodiment, a method comprises acquiring, via an imaging system, projection data for a plurality of x-ray spectra, estimating path lengths for a plurality of materials based on the projection data and calibration data for the imaging system, iteratively refining the estimated path lengths based on a linearized model derived from the calibration data, and reconstructing material-density images for each material of the plurality of materials from the iteratively-refined estimated path lengths. By determining path-length estimates in this way without modeling the physics of the imaging system, accurate material decomposition may be performed more quickly and with less sensitivity to changes in physics of the system, and furthermore may be extended to more than two materials.

20 Claims, 8 Drawing Sheets

(56) References Cited

OTHER PUBLICATIONS

Kis, B.J., et al.: "Single-energy material decomposition using X-ray path length estimation", Journal of Computer Assisted Tomography, vol. 36, No. 6, 2012, pp. 768-777, XP009530846, p. 769, right-hand column, paragraph 3—p. 772, left-hand column, paragraph 2.
Zhao Wei et al: "A unified material decomposition framework for quantitative dual- and triple-energy CT imaging", Medical Physics, vol. 45, No. 7, May 18, 2018 (May 18, 2018), pp. 2964-2977, XP55855114, p. 2966, left-hand column, paragraph 3.

* cited by examiner

METHODS AND SYSTEMS FOR MULTI-MATERIAL DECOMPOSITION

FIELD

Embodiments of the subject matter disclosed herein relate to computed tomography (CT) imaging, and more specifically to multi-material decomposition for CT imaging.

BACKGROUND

Dual or multi-energy spectral computed tomography (CT) imaging systems can reveal the densities of different materials in an object and generate images corresponding to multiple monochromatic x-ray energy levels. A CT imaging system can derive the behavior at different monochromatic energy levels based on signals from at least two regions of photon energy in the spectrum, e.g., the low-energy and the high-energy portions of the incident x-ray spectrum. In a given energy region for medical CT, wherein the object being scanned is a patient, two physical processes dominate x-ray attenuation processes: Compton scattering and the photoelectric effect. The detected signals from two energy regions provide sufficient information to resolve the energy dependence on the material being imaged. Detected signals from the two energy regions provide sufficient information to determine the relative composition of an object composed of two hypothetical materials.

BRIEF DESCRIPTION

In one embodiment, a method comprises acquiring, via an imaging system, projection data for a plurality of x-ray spectra, estimating path lengths for a plurality of materials based on the acquired projection data and calibration data for the imaging system, and reconstructing material-density images for each material of the plurality of materials from the estimated path lengths. Hereinafter, the term "path length" is used to specify the line integral of the material-density images along a line connecting the x-ray source to individual detector elements. By determining path-length estimates in this way without modeling the physics of the imaging system, accurate material decomposition may be performed more quickly and with less sensitivity to changes in physics of the system, and furthermore may be extended to more than two materials.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
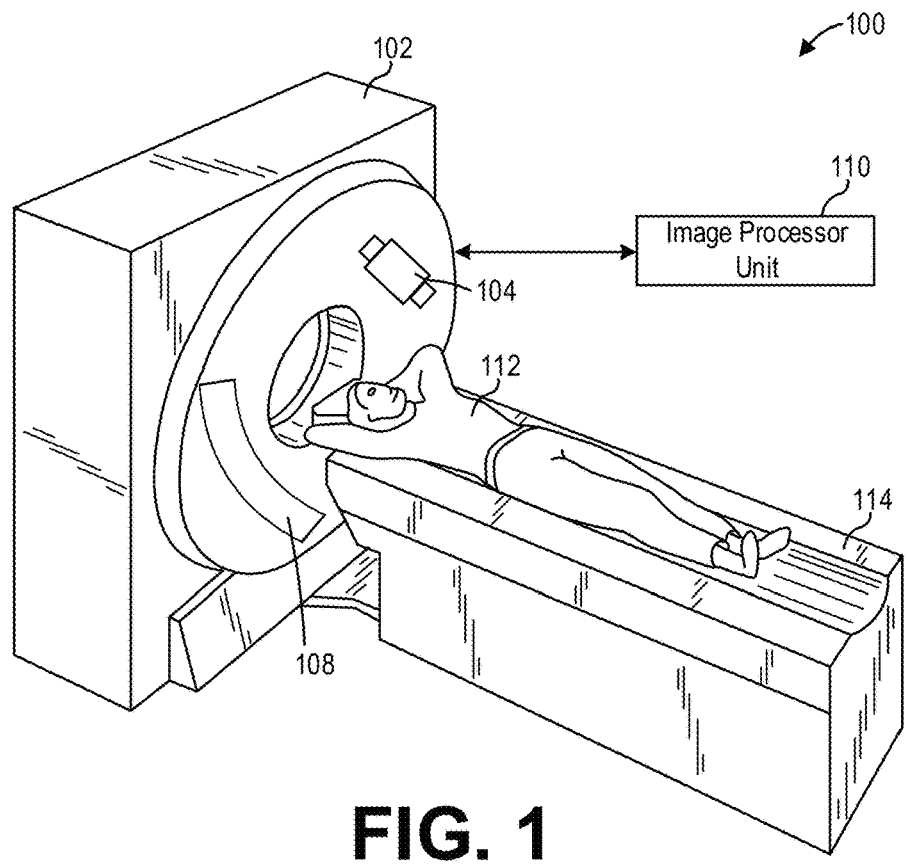
FIG. 1 shows a pictorial view of an imaging system, according to an embodiment.
Figure 2:
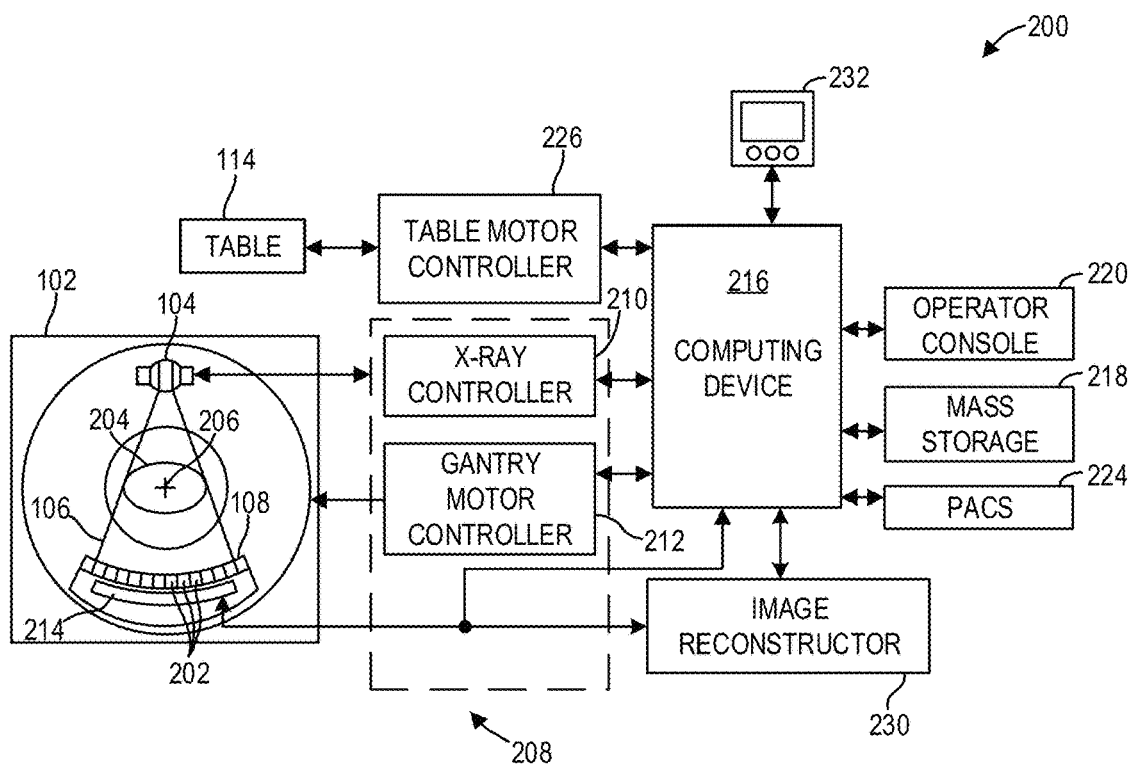
FIG. 2 shows a block schematic diagram of an exemplary imaging system, according to an embodiment.

The following description relates to various embodiments of spectral computed tomography (CT) imaging. In particular, methods and systems for multi-material decomposition in spectral CT imaging are provided. An example of a CT imaging system that may be used to acquire images in accordance with the present techniques is shown in FIGS. 1 and 2. The CT imaging system may be configured with energy-discriminating detectors such as photon-counting detectors, which provide the fidelity to discriminate materials via material decomposition. Material decomposition may be performed in the projection domain, the image domain, or jointly with reconstruction. However, the joint material decomposition-reconstruction approach is usually computationally expensive compared to both projection- and image-domain approaches. Further, projection domain methods for multi-material decomposition (i.e., material decomposition for two or more materials) typically depends on prior knowledge of the imaging system, such as knowledge of some model of the effective x-ray spectra, which generally is a combination of the x-ray spectra and the detector spectral response. Such prior knowledge is difficult to obtain in practice with a high degree of precision, especially if the detector spectral response varies across the detector array and/or when the emitted x-ray spectra change with x-ray tube life. A method for multi-material decomposition, such as the method depicted in FIG. 3, overcomes the challenges of these previous approaches by estimating multi-material path lengths based only on calibration data and without the need for knowledge of the physics of the multi-energy CT imaging system. The method includes a two-step technique, wherein a preliminary estimate is first obtained based on calibration data and acquired projection data, and then the preliminary estimate is used to initialize an iterative scheme that optimizes a statistical criterion to further enhance the accuracy, in a statistical sense, of the multi-material path lengths. A method for obtaining the preliminary estimate of the multi-material path lengths, as shown in FIG. 4, includes a combination of a functional inverse look-up and local multi-linear-fit approaches. The process of calculating such preliminary estimates is illustrated with simulated data in FIGS. 5 and 6. The results of further simulations, shown in FIGS. 7-9, indicate that the preliminary estimate is highly accurate, such that the iterative scheme can obtain final estimates of multi-material path lengths to an even higher degree of accuracy with only a few iterations. The methods described herein for directly estimating multi-material path lengths may also be adapted to estimate monochromatic sinograms at multiple energies, as shown in FIG. 10.

FIG. 1 illustrates an exemplary CT system 100 configured for CT imaging. Particularly, the CT system 100 is configured to image a subject 112 such as a patient, an inanimate object, one or more manufactured parts, and/or foreign objects such as dental implants, stents, and/or contrast agents present within the body. In one embodiment, the CT system 100 includes a gantry 102, which in turn, may further include at least one x-ray source 104 configured to project a beam of x-ray radiation 106 (see FIG. 2) for use in imaging the subject 112 laying on a table 114. Specifically, the x-ray source 104 is configured to project the x-ray radiation beams 106 towards a detector array 108 positioned on the opposite side of the gantry 102. Although FIG. 1 depicts only a single x-ray source 104, in certain embodiments, multiple x-ray sources and detectors may be employed to project a plurality of x-ray radiation beams 106 for acquiring projection data at different energy levels corresponding to the patient. In some embodiments, the x-ray source 104 may enable dual-energy spectral imaging by rapid peak kilovoltage (kVp) switching. In some embodiments, the x-ray detector employed is a photon-counting detector which is capable of differentiating x-ray photons of different energies. In other embodiments, two sets of x-ray sources and detectors are used to generate dual-energy projections, with one operating at low-kVp and the other at high-kVp. It should thus be appreciated that the methods described herein may be implemented with a variety of multi-spectral acquisition techniques, and is not limited to the specific described embodiments.

In certain embodiments, the CT system 100 further includes an image processor unit 110 configured to reconstruct images of a target volume of the subject 112 using an iterative or analytic image reconstruction method. For example, the image processor unit 110 may use an analytic image reconstruction approach such as filtered back-projection (FBP) to reconstruct images of a target volume of the patient. As another example, the image processor unit 110 may use an iterative image reconstruction approach such as advanced statistical iterative reconstruction (ASIR), conjugate gradient (CG), maximum likelihood expectation maximization (MLEM), model-based iterative reconstruction (MBIR), and so on, to reconstruct images of a target volume of the subject 112. As described further herein, in some examples the image processor unit 110 may use both an analytic image reconstruction approach such as FBP in addition to an iterative image reconstruction approach.

In some CT imaging system configurations, an x-ray source projects a cone-shaped x-ray radiation beam which is collimated to lie within an X-Y-Z plane of a Cartesian coordinate system and generally referred to as an "imaging plane." The x-ray radiation beam passes through an object being imaged, such as the patient or subject. The x-ray radiation beam, after being attenuated by the object, impinges upon an array of detector elements. The intensity of the attenuated x-ray radiation beam received at the detector array is dependent upon the attenuation of a radiation beam by the object. Each detector element of the array produces a separate electrical signal that is a measurement of the x-ray beam attenuation at the detector location. The attenuation measurements from all the detector elements are acquired separately to produce a transmission profile.

In some CT systems, the x-ray source and the detector array are rotated with a gantry within the imaging plane and around the object to be imaged such that an angle at which the radiation beam intersects the object constantly changes. A group of x-ray radiation attenuation measurements, e.g., projection data, from the detector array at one gantry angle is referred to as a "view." A "scan" of the object includes a set of views made at different gantry angles, or view angles, during one revolution of the x-ray source and detector. It is contemplated that the benefits of the methods described herein accrue to medical imaging modalities other than CT, so as used herein the term "view" is not limited to the use as described above with respect to projection data from one gantry angle. The term "view" is used to mean one data acquisition whenever there are multiple data acquisitions from different angles, whether from a CT imaging system or another imaging system acquiring multi-spectral attenuation measurements.

The projection data is processed to reconstruct an image that corresponds to a two-dimensional slice taken through the object or, in some examples where the projection data includes data from multiple detector rows or from multiple gantry rotations, a three-dimensional volumetric representation of the object. One method for reconstructing an image from a set of projection data is referred to in the art as the filtered back projection technique. Transmission and emission tomography reconstruction techniques also include statistical iterative methods such as maximum likelihood expectation maximization (MLEM) and ordered-subsets expectation-reconstruction techniques as well as iterative reconstruction techniques. This process converts the attenuation measurements from a scan into "CT numbers" or "Hounsfield units," which are used to control the brightness of a corresponding pixel on a display device.

To reduce the total scan time, a "helical" scan may be performed. To perform a "helical" scan, the patient is moved using the table 114 while the data for the prescribed number of slices is acquired. Such a system generates a single helix from a cone beam helical scan. The helix mapped out by the cone beam yields projection data from which images in each prescribed slice may be reconstructed.

As used herein, the phrase "reconstructing an image" is not intended to exclude embodiments of the present invention in which data representing an image is generated but a viewable image is not. Therefore, as used herein, the term "image" broadly refers to both viewable images and data representing a viewable image. However, many embodiments generate (or are configured to generate) at least one viewable image. As used herein, the term image may refer to a two-dimensional image as well as to a three- or higher-dimensional image volume.

FIG. 2 illustrates an exemplary imaging system 200 similar to the CT system 100 of FIG. 1. In accordance with aspects of the present disclosure, the imaging system 200 is configured for imaging a subject 204 (e.g., the subject 112 of FIG. 1). In one embodiment, the imaging system 200 includes the detector array 108 (see FIG. 1). The detector array 108 further includes a plurality of detector elements 202 that together sense the x-ray radiation beam 106 (see FIG. 2) that pass through the subject 204 (such as a patient) to acquire corresponding projection data. Accordingly, in one embodiment, the detector array 108 is fabricated in a multi-slice configuration including the plurality of rows of cells or detector elements 202. In such a configuration, one or more additional rows of the detector elements 202 are arranged in a parallel configuration for acquiring the projection data.

In certain embodiments, the imaging system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

As the x-ray source 104 and the detector array 108 rotate, the detector array 108 collects data of the attenuated x-ray beams. The data collected by the detector array 108 undergoes pre-processing and calibration to condition the data to represent the line integrals of the attenuation coefficients of the scanned subject 204. The processed data are commonly called projections.

In some examples, the individual detectors or detector elements 202 of the detector array 108 may include energy-discriminating photon-counting detectors which register the interactions of individual photons into one or more energy bins. It should be appreciated that the methods described herein may also be implemented with energy-integrating detectors.

The acquired sets of projection data may be used for basis material decomposition (BMD). During BMD, the measured projections are converted to a set of material-density projections. The material-density projections may be reconstructed to form a pair or a set of material-density maps or images—a map or image of each respective basis material, such as bone, soft tissue, and/or contrast agent maps. The density maps or images may be, in turn, associated to form a volume rendering of the basis material, for example, bone, soft tissue, and/or contrast agent, in the imaged volume.

Once reconstructed, the basis material image produced by the imaging system 200 reveals internal features of the subject 204, expressed in the densities of two basis materials. The density image may be displayed to show these features. In traditional approaches for diagnosis of medical conditions, such as disease states, and more generally of medical events, a radiologist or physician would consider a hard copy or display of the density image to discern characteristic features of interest. Such features might include lesions, sizes and shapes of particular anatomies or organs, and other features that would be discernable in the image based upon the skill and knowledge of the individual practitioner.

In one embodiment, the imaging system 200 includes a control mechanism 208 to control movement of the components such as rotation of the gantry 102 and the operation of the x-ray source 104. In certain embodiments, the control mechanism 208 further includes an x-ray controller 210 configured to provide power and timing signals to the x-ray source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The DAS 214 may comprise a component of the control mechanism 208, or a separate component, as shown in FIG. 2. The DAS 214 may be further configured to selectively aggregate analog data from a subset of the detector elements 202 into so-called macro-detectors, as described further herein. The data sampled and digitized by the DAS 214 is transmitted to a computer or computing device 216. In one example, the computing device 216 stores the data in a storage device or mass storage 218. The storage device 218, for example, may include a hard disk drive, a floppy disk drive, a compact disk-read/write (CD-R/W) drive, a Digital Versatile Disc (DVD) drive, a flash drive, and/or a solid-state storage drive.

Additionally, the computing device 216 provides commands and parameters to one or more of the DAS 214, the x-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen to allow the operator to specify the commands and/or scanning parameters.

Although FIG. 2 illustrates only one operator console 220, more than one operator console may be coupled to the imaging system 200, for example, for inputting or outputting system parameters, requesting examinations, plotting data, and/or viewing images. Further, in certain embodiments, the imaging system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks, wireless telephone networks, wireless local area networks, wired local area networks, wireless wide area networks, wired wide area networks, etc.

In one embodiment, for example, the imaging system 200 either includes, or is coupled to, a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which in turn, may control a table 114 which may be a motorized table. Specifically, the table motor controller 226 may move the table 114 for appropriately positioning the subject 204 in the gantry 102 for acquiring projection data corresponding to the target volume of the subject 204.

As previously noted, the DAS 214 samples and digitizes the projection data acquired by the detector elements 202. Subsequently, an image reconstructor 230 uses the sampled and digitized x-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the imaging system 200 and instead the computing device 216 may perform one or more functions of the image reconstructor 230. Moreover, the image reconstructor 230 may be located locally or remotely, and may be operatively connected to the imaging system 200 using a wired or wireless network. Particularly, one exemplary embodiment may use computing resources in a "cloud" network cluster for the image reconstructor 230.

In one embodiment, the image reconstructor 230 stores the images reconstructed in the storage device 218. Alternatively, the image reconstructor 230 may transmit the reconstructed images to the computing device 216 for generating useful patient information for diagnosis and evaluation. In certain embodiments, the computing device 216 may transmit the reconstructed images and/or the patient information to a display or display device 232 communicatively coupled to the computing device 216 and/or the image reconstructor 230. In some embodiments, the reconstructed images may be transmitted from the computing device 216 or the image reconstructor 230 to the storage device 218 for short-term or long-term storage.

The various methods and processes (such as the methods described below with reference to FIGS. 3, 4, and 10) described further herein may be stored as executable instructions in non-transitory memory on a computing device (or controller) in imaging system 200. In one embodiment, image reconstructor 230 may include such executable instructions in non-transitory memory, and may apply the methods described herein to reconstruct an image from scanning data. In another embodiment, computing device 216 may include the instructions in non-transitory memory, and may apply the methods described herein, at least in part, to a reconstructed image after receiving the reconstructed image from image reconstructor 230. In yet another embodiment, the methods and processes described herein may be distributed across image reconstructor 230 and computing device 216.

In one embodiment, the display 232 allows the operator to evaluate the imaged anatomy. The display 232 may also allow the operator to select a volume of interest (VOI) and/or request patient information, for example, via a graphical user interface (GUI) for a subsequent scan or processing.

Figure 3:
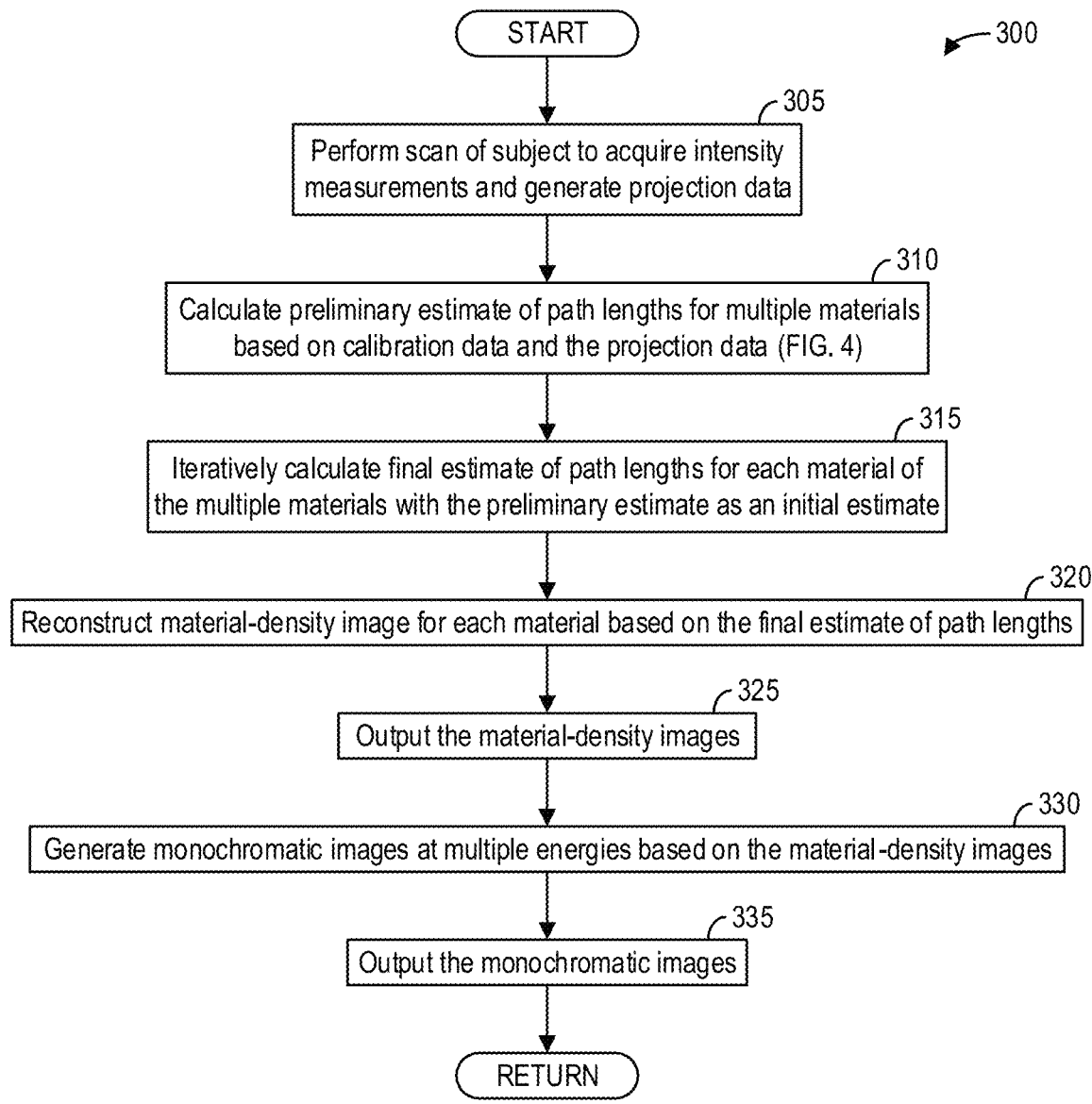
FIG. 3 shows a high-level flow chart illustrating an example method for multi-material decomposition according to an embodiment.
Figure 4:
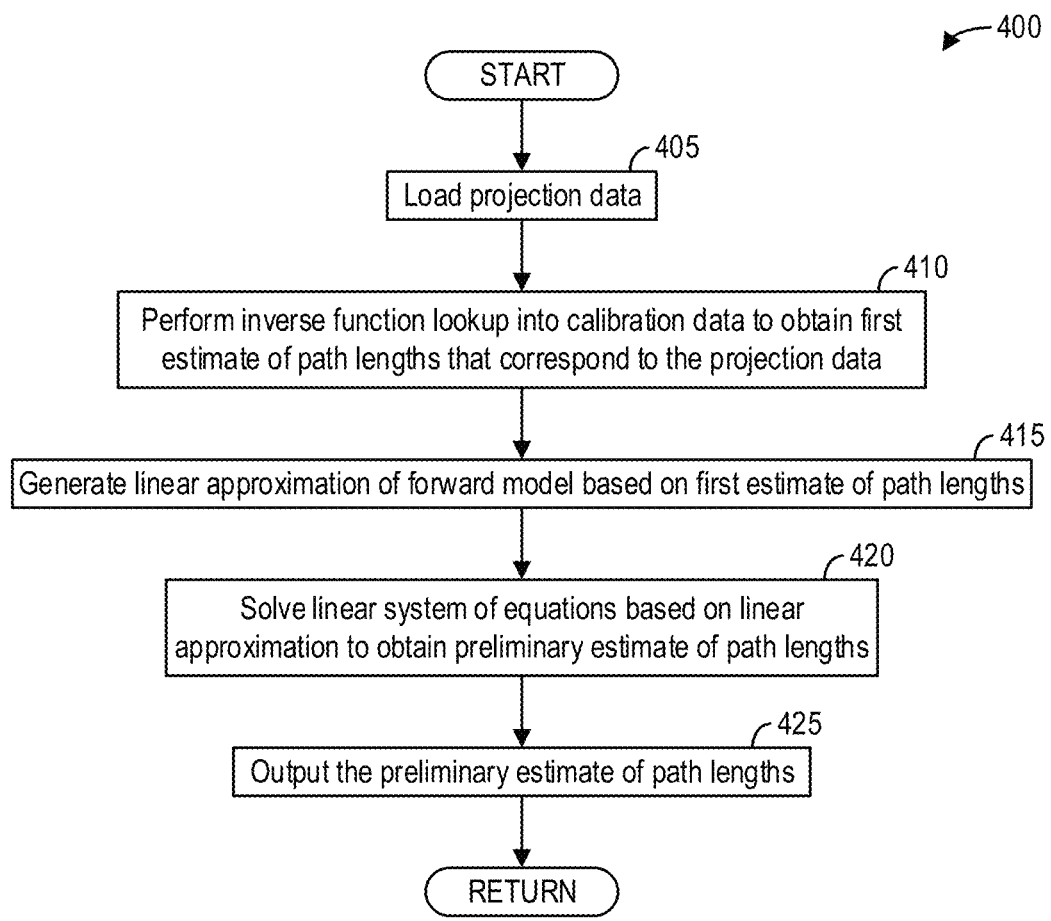
FIG. 4 shows a high-level flow chart illustrating an example method for calculating a preliminary estimate of path lengths for multiple materials based on calibration data according to an embodiment.

FIG. 3 shows a high-level flow chart illustrating an example method 300 for multi-material decomposition according to an embodiment. In particular, method 300 relates to performing multi-material decomposition in the projection domain based on calibration data rather than based on knowledge of physics of the imaging system, such as a model of the incident x-ray spectra and/or of the detector response. Method 300 is described with regard to the systems and components of FIGS. 1 and 2, though it should be appreciated that the method 300 may be implemented with other systems and components without departing from the scope of the present disclosure. Method 300 may be implemented as executable instructions in non-transitory memory of the computing device 216 and/or the image reconstructor 230, for example, and may be executed by a processor of the computing device 216 and/or the image reconstructor 230 to perform the actions described herein.

Method 300 begins at 305. At 305, method 300 performs a scan of a subject to acquire intensity measurements and generate projection data. The scan comprises a dual-energy CT scan or a multi-energy CT scan of the subject. To that end, method 300 controls the x-ray controller 210 to drive the x-ray source 104 to emit x-rays at two or more energy levels, for example, while also controlling the gantry motor controller 212 and the table motor controller 226 to adjust positions of the gantry 102 and the table 114, respectively, such that the position of the x-ray source 104 relative to the subject 204 being scanned is adjusted while generating the x-rays. Method 300 further acquires, via the DAS 214 for example, the projection data measured by energy-discriminating detectors including photon-counting detectors, such as the detector elements 202 of the detector array 108. The projection data comprises multi-energy photon-count measurements, for example, wherein the measurements of photons of different energies are sorted into predefined energy bins.

At 310, method 300 calculates a preliminary estimate of path lengths for multiple materials based on calibration data and the projection data. The calibration data comprises calibration data for calibrating the imaging system that is acquired during a calibration scan, with the imaging system, of a phantom comprising known materials and known path lengths. Method 300 calculates a preliminary estimate of path lengths for multiple materials, based on the calibration data, which would result in the observed multi-energy measurements of the projection data. To that end, method 300 may perform a two-step estimation that performs an inverse function lookup into the calibration data to obtain an initial estimate of multi-material path lengths that would result in the observed multi-energy measurement, and refining the initial estimate by solving a linear system of equations constructed based on the initial estimate. An example method for calculating a preliminary estimate of path lengths for multiple materials based on calibration data is described further herein with regard to FIG. 4.

At 315, method 300 iteratively calculates a final estimate of path lengths for each material of the multiple materials with the preliminary estimate as an initial estimate. For example, method 300 may calculate a final estimate $m^{final}$ by iteratively solving the equation:

$$m^{final} = \operatorname*{argmin}_{m} F[m, f^{cal}(m), p^{meas}, I^{meas}],$$

subject to $m \in \Omega_m$, wherein $\Omega_m$ comprises a set of (physically) feasible material-path-length vectors, F is a statistical criterion (e.g., the log-likelihood) that when optimized produces a (physically) meaningful estimate of multi-material path lengths, $f^{cal}$ comprises a differentiable forward model that maps known material path lengths to correspondingly known projection values (p-values) or x-ray intensities (I-values), using interpolants or polynomial models, $p^{meas}$ comprises the p-values measured at 305, and $I^{meas}$ comprises the x-ray intensities measured at 305. While the formulation above applies to the entire sinogram (i.e., all sinogram bins i), it should be appreciated that, depending on the components of F, the equation above for the final estimate $m^{final}$ may be separable in the sinogram bins i and thus may be solved in parallel.

The statistical problem above may be understood as setting up a maximum-likelihood (or maximum a posteriori) estimator for the desired multi-material path lengths. In one example, the function F may comprise a Poisson log-likelihood function, such that:

$$F[m, f_i^{cal}(m), I^{meas}] = \sum_{i,k} \frac{I_{i,k}^{meas}}{I_{0i,k}^{meas}} \times \log(f_{i,k}^{cal}(m)) - f_{i,k}^{cal}(m),$$

where the index i indexes sinogram bins, the index k indexes energy bins, the measured x-ray intensities $I_{0\ i,k}^{meas}$ correspond to an air scan in the absence of materials, $f_{I_{i,k}}^{cal}(m)$ is a differentiable forward model that maps known material path lengths to known normalized x-ray intensities $I_{i,k}^{cal}/I_{0\ i,k}^{cal}$, where $I_{i,k}^{cal}$ and $I_{0\ i,k}^{cal}$ correspond respectively to calibration intensity measurements and an air scan in the absence of materials. In another example, the function F may comprise a weighted least-squares criterion function, such that:

$$F[m, f_p^{cal}(m), p^{meas}] = \Sigma_i \|f_{p_i}^{cal}(m) - p_i^{meas}\|_{w_i^{meas}}^2,$$

where $W_i^{meas}$ is proportional to $I_i^{meas}$, and $f_{p_i}^{cal}(m)$ is a differentiable forward model that maps known path lengths to known p-values and the index i indexes sinogram bins. An advantage for using the Poisson log-likelihood function for F is that this function is more effective in scenarios where the measured x-ray intensities $I^{meas}$ are low (or even zero, in the case of photon-counting detectors, or negative due to electronic noise, in the case of energy-integrating detectors) which prevents the application of $-\log(\bullet)$ in computing $p^{meas}$, where a component $p_{i,k}^{meas}$ of $p^{meas}$ corresponding to sinogram-bin index i and energy-bin index k is computed as:

$$p_{i,k}^{meas} = -\log\left(\frac{I_{i,k}^{meas}}{I_{0i,k}^{meas}}\right).$$

At 320, method 300 reconstructs a material-density image for each material based on the final estimate of path lengths. For example, the final estimate of path lengths for each material comprise material-basis projections, and so method 300 thus reconstructs a material-density image for each material from the final path-length estimates for the material. At 325, method 300 outputs the material-density images. For example, method 300 may output the material-density images to a display device, such as the display device 232. Additionally or alternatively, method 300 may output the material-density images to mass storage 218 for storage and/or PACS 224 for remote review.

At 330, method 300 generates monochromatic images at multiple energies based on the material-density images. For example, method 300 may selectively combine the material-density images to generate a monochromatic images at a given energy which emulate an acquisition using an x-ray source emitting photons only at the given energy. Method 300 may generate a plurality of monochromatic images at different energies from the material-density images. At 335, method 300 outputs the monochromatic images. For example, method 300 may output the monochromatic images to a display device, such as the display device 232. Additionally or alternatively, method 300 may output the material-density images to mass storage 218 for storage and/or PACS 224 for remote review. Method 300 then returns.

FIG. 4 shows a high-level flow chart illustrating an example method 400 for calculating a preliminary estimate of path lengths for multiple materials based on calibration data according to an embodiment. In particular, method 400 relates to determining a first estimate of path lengths based on calibration data, and refining the first estimate by solving a linear system of equations that correspond to a local linear approximation of the forward model at the first estimate. Method 400 is described with regard to the systems and components of FIGS. 1 and 2, though it should be appreciated that the method 400 may be implemented with other systems and components without departing from the scope of the present disclosure. Method 400 may be implemented as executable instructions in non-transitory memory of the computing device 216 and/or the image reconstructor 230, for example, and may be executed by a processor of the computing device 216 and/or the image reconstructor 230 to perform the actions described herein. Method 400 may comprise a sub-routine of method 300, and specifically may comprise the action 310 of calculating a preliminary estimate of path lengths for multiple materials based on calibration data and projection data.

Method 400 begins at 405. At 405, method 400 loads projection data. For example, method 400 loads the projection data acquired at 305 as described hereinabove. The projection data comprises multi-energy photon-count measurements, for example, wherein the measurements of photons of different energies are sorted into predefined energy bins.

Continuing at 410, method 400 performs an inverse function lookup into calibration data to obtain a first estimate of path lengths that correspond to the projection data. The calibration data comprises measurements acquired during a calibration scan for calibrating the imaging system using a phantom comprising known materials and known path lengths. For example, the calibration data may be stored in non-transitory memory as a set $S^{cal}$:

$$S^{cal} = \{(m_{ij}^{cal}, p_{ij}^{cal}), i=1,2,\ldots, j=1,2,\ldots\},$$

where each vector $m_{ij}^{cal} = [m_{ij1}^{cal}, \ldots, m_{ijL}^{cal}]$ is a L×1 vector of known path lengths of L materials, each vector $p_{ij}^{cal} = [p_{ij1}^{cal}, \ldots, p_{ijL}^{cal}]$ is a K×1 vector of known p-values (log-normalized intensity values) corresponding to $k=1,\ldots,K$ energy bins, i is the sinogram-bin index, and j is the experiment index where different experiments correspond to different material combinations. A differentiable forward model $f_{p_i}^{cal}(m)$ for the ith sinogram bin is constructed based on the calibration set $S^{cal}$ that maps material path lengths m to p-values such that, using interpolants such as non-uniform rational B-splines or Lagrange interpolants, $$f_{p_i}^{cal}(m_{ij}^{cal}) = p_{ij}^{cal},$$

or alternatively, using polynomial models, $$f_{p_i}^{cal}(m_{ij}^{cal}) \approx p_{ij}^{cal}.$$

Then, for a given K-energy-bin log-normalized measurement vector, $$p_i^{meas} = [p_{i1}^{meas}, \ldots, p_{iK}^{meas}],$$

and a respective x-ray intensity measurement vector, $$I_i^{meas} = [I_{i1}^{meas}, \ldots, I_{iK}^{meas}],$$

corresponding to a sinogram-bin i (i.e., corresponding to one x-ray projection line), method 400 finds possible candidate vectors $m_{ij}^{cal}$ from the calibration data $S^{cal}$ that result in a p-value vector $p_{ij}^{cal}$ that is close to the measurement vector $p_i^{meas}$. For example, method 400 may determine:

$$S^{lookup} = \{m_{ij}^{cal} : K \geq [\Sigma_{k=1}^{K} 1_{dist(p_{ij}^{cal}, p_k^{meas}) \leq T_p}] \geq K_{sub}\},$$

where the function $1_{(\cdot)}$ is an indicator function that is unity (i.e., one) if the condition in the parentheses is met or zero otherwise, $3 \leq K_{sub} \leq K$, $T_p$ is a prescribed threshold for nearness of $p_i^{meas}$ to $p_{ij}^{cal}$, and the function dist(a, b) is a function that measures the distance between its arguments a and b. In some examples, the function dist(a, b) may comprise absolute-difference or squared-difference functions. The resulting set of lookup results, $$S^{lookup} = \{m_{i1}^{cal}, \ldots, m_{iN}^{cal}\},$$

thus comprises a set of material vectors from which method 400 obtains a rough estimate of the desired multi-material path lengths. For example, method 400 calculates the initial estimate by performing a simple weighted sum of the material vectors:

$$m_i^{lookup} = \frac{\sum_{n=1}^{N} w_n \times m_{in}^{cal}}{\sum_{n=1}^{N} w_n},$$

where $w_n$ comprise weights that give higher priority to material path lengths $m_{in}^{cal}$ whose corresponding p-value vector $p_{ij}^{cal}$ is numerically closer to $p_i^{meas}$. The numerical closeness depends on the truth-worthiness of the measured p-value $p_{ik}^{meas}$ in the vector $p_i^{meas}$, which in turn is decided based on the corresponding x-ray intensity measurement $I_{ik}^{meas}$ in the intensity measurement vector $I_i^{meas}$, wherein the higher the intensity, the higher the trust. The weighting model thus provides a statistically-relevant estimation by giving higher weight to energy bins with higher detected x-ray intensity.

At 415, method 400 generates a linear approximation of the forward model based on the first estimate of path lengths. For example, method 400 may further refine the first estimate $m_i^{lookup}$ by performing a local multi-linear approximation modeling of the forward model $f_{p_i}^{cal}$ of the calibration data around the first estimate $m_i^{lookup}$. This multi-linear approximation model results in a linear system of equations that may be expressed as:

$$M_i^{cal} \times C_i^{fit} = P_i^{cal},$$

where the coefficient matrix $C_i^{fit}$ comprises the coefficients of the linear model that are obtained by solving the above linear system for a known set of $p_{ij}^{cal}$ stacked in the matrix $P_i^{cal}$ corresponding to known path lengths (i.e., $m_{ij}^{cal}$) stacked as multi-linear basis vectors, one for each material, in the matrix $M_i^{cal}$. Note that in the following paragraphs, the vectors $m_i$ and $p_i$ are now representing linearizations around the operating point defined by the look-up step. After determining the coefficient matrix, method 400 then generates the linear approximation of the forward model based on the first estimate of the path lengths by setting up a similar linear system for the vector of measured p-values $p_i^{meas}$ such that:

$$m_i^{prelim} \times C_i^{fit} = p_i^{meas}.$$

Continuing at 420, method 400 solves the linear system of equations based on the linear approximation to obtain a preliminary estimate of path lengths. For example, to solve the linear system established above for the preliminary estimate $m_i^{prelim}$ of path lengths, method 400 calculates:

$$m_i^{prelim} = p_i^{meas} \times W_{i,J_{meas}} [C_i^{fit}]^T \times [C_i^{fit} W_{i,J_{meas}} [C_i^{fit}]^T]^{-1},$$

where the weighting matrix $W_{i,J_{meas}}$ is proportional to the measured intensities $I_i^{meas}$ to give relatively better weighting to energy bins with a higher measured x-ray intensity.

Figure 6:
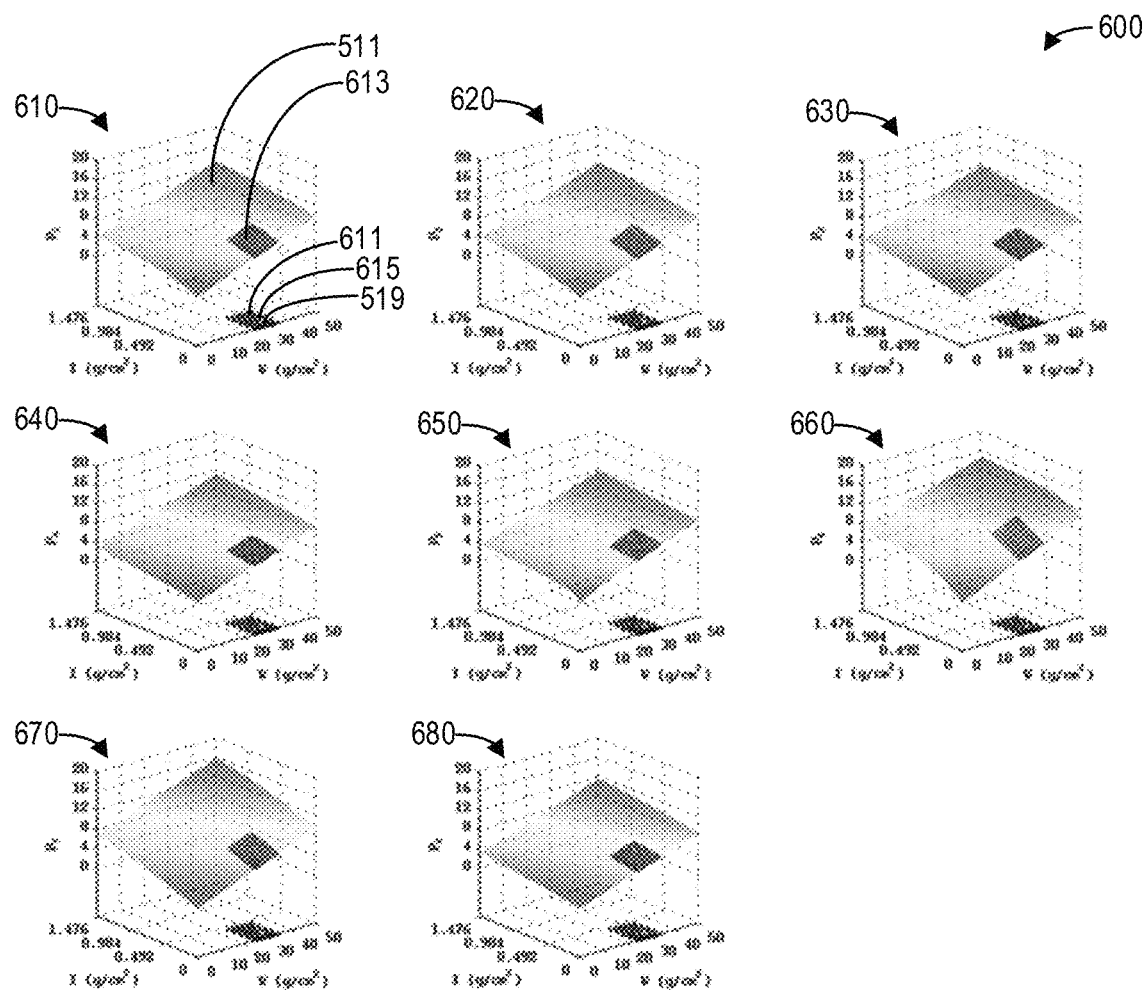
FIG. 6 shows a set of graphs depicting example linear models for refining initial estimates of path lengths for multiple materials according to an embodiment.

An illustrative example of local linear models of the forward model constructed based on the first estimate of path lengths is described further herein with regard to FIG. 6.

At 425, method 400 outputs the preliminary estimate of path lengths. For example, method 400 may output the preliminary estimate of path lengths to memory, such that method 300 may iteratively calculate the final estimate of path lengths for each material with the preliminary estimate as an initial estimate, as described hereinabove. Method 400 then returns.

Figure 5:
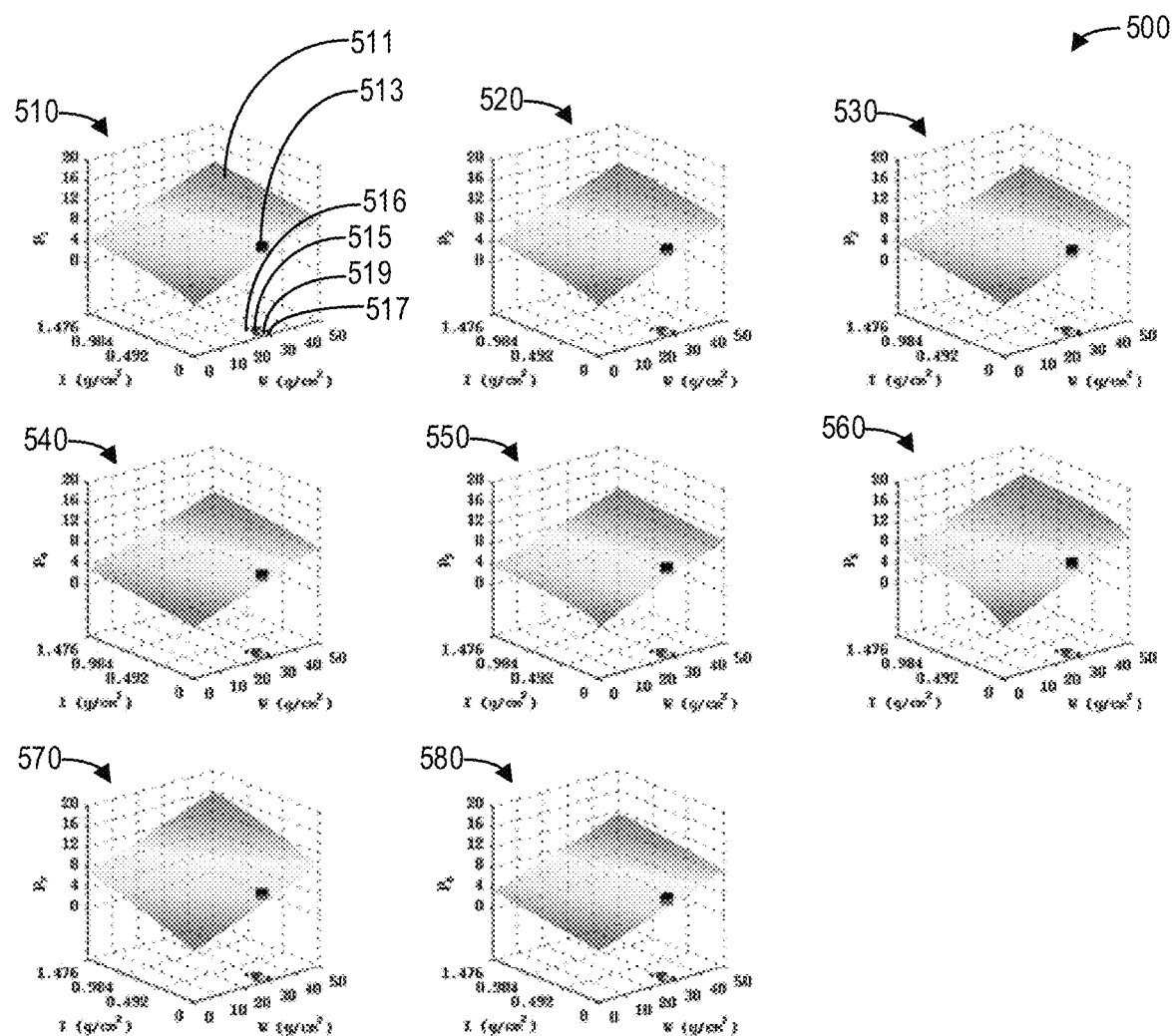
FIG. 5 shows a set of graphs depicting example multi-dimensional surfaces for initially estimating path lengths for multiple materials according to an embodiment.

FIG. 5 shows a set of graphs 500 depicting example multi-dimensional surfaces for initially estimating path lengths for multiple materials according to an embodiment. The set of graphs 500 includes a graph for each energy bin of a plurality of energy bins, specifically K=8 spectral energy bins in the depicted example, including a first graph 510 for a first energy bin, a second graph 520 for a second energy bin, a third graph 530 for a third energy bin, a fourth graph 540 for a fourth energy bin, a fifth graph 550 for a fifth energy bin, a sixth graph 560 for a sixth energy bin, a seventh graph 570 for a seventh energy bin, and an eighth graph 580 for an eighth energy bin. Each graph of the set of graphs 500 depicts a plot of a surface of a forward model (for example, $f_{p_i}^{cal}$) that maps material path lengths (for example, $m_{ij}^{cal}$) to log-normalized calibration data (for example, $p_{ij}^{cal}$).

For example, the first graph 510 illustrates a first surface 511 of a forward model that maps material path lengths to log-normalized calibration data $p_{ij1}$ for the first energy bin (e.g., k=1) of a photon-counting CT imaging system. Specifically, the first surface 511 maps material path lengths for two materials, water (W) and iodine (I), to the calibration data. The black dots on each surface including the first surface 511 correspond to measurements $p_i^{meas}$ along an x-ray path, including a measurement 513 (e.g., $p_1^{meas}$). The dots 516 and 517 on the [W, I] plane represent potential estimates $m_{ij}^{cal}$ of [W, I] path lengths, which are derived jointly from plots 510, 520, 530, 540, 550, 560, 570, and 580, for instance, using the $S^{lookup}$ criterion, and from which a first estimate 515 (e.g. $m_i^{lookup}$) of [W, I] path lengths for materials along the x-ray path corresponding to the above measurement $p_i^{meas}$ (i.e., the 8×1 vector of values in the depicted example) is derived as described hereinabove. The dot 519 indicates the ground truth or the actual path lengths for the materials.

The preliminary estimate 515 is in the [W, I] plane and represents the estimated Water and Iodine path lengths corresponding to a measurement $p_i^{meas}$. The preliminary estimate 515 is thus, for illustrative purposes, replicated in all plots 520, 530, 540, 550, 560, 570, and 580. It should be appreciated that two materials, water and iodine, are depicted for ease of illustration, as the dimensionality of a forward model for three or more materials is difficult to illustrate in a two-dimensional representation. Nevertheless, the illustrated method is applicable to two or more materials.

To improve the first estimate obtained from the surfaces of the forward model depicted in FIG. 5, a local joint linear model of the surfaces may be constructed. As an illustrative and non-limiting example, FIG. 6 shows a set of graphs 600 depicting example linear models for refining the initial estimates of path lengths for multiple materials depicted in the set of graphs 500 of FIG. 5.

The set of graphs 600 includes a first graph 610 for the first energy bin, a second graph 620 for the second energy bin, a third graph 630 for the third energy bin, a fourth graph 640 for the fourth energy bin, a fifth graph 650 for the fifth energy bin, a sixth graph 660 for the sixth energy bin, a seventh graph 670 for the seventh energy bin, and an eighth graph 680 for the eighth energy bin. Each graph of the set of graphs 600 depicts the surfaces of the forward model $f_{p_i}^{cal}$, depicted in the set of graphs 500, including the first surface 511.

Based on each estimate for each energy bin obtained as depicted in FIG. 5, a local joint linear model of each surface is constructed, resulting in a linear system of equations that may be solved to obtain an improved estimate over the first estimate. For example, based on the first estimate 515, a linear model 613 of the surface 511 is constructed to correspond to the region 611 of the [W, I] plane used for constructing the linear model 613 as described hereinabove. The linear model 613 together with the linear models in 620, 630, 640, 650, 660, 670, and 680 results in a joint linear system of equations that can be solved to find a better, preliminary estimate 615 indicated in the plot 610 (e.g., $m_i^{prelim}$) of the path lengths relative to the first estimate 515. Note that the preliminary estimate 615 is in the [W, I] plane and represents the estimated Water and Iodine path lengths. The preliminary estimate 615 is thus, for illustrative purposes, replicated in all plots 620, 630, 640, 650, 660, 670, and 680. In particular, the preliminary estimate 615 is closer to the ground truth 519 than the first estimate 515.

Alternatively, both the first estimate (e.g., $m_i^{lookup}$) and the improved estimate (e.g., $m_i^{prelim}$) can be obtained by using an intensity-domain forward model $f_{I_i}^{cal}$ that maps known material path lengths to known x-ray intensity values $I_i^{cal}$ by suitably modifying the hereinabove described method 400 to use the intensity domain calibration and measured data, $I_i^{cal}$ and $I_i^{meas}$, respectively. Working in the intensity domain can be advantageous especially if $I_i^{meas}$ has poor signal-to-noise ratio or if $I_i^{meas}$ non-positive.

The preliminary estimate thus obtained is used to initialize the iterative optimizer (for example, as described hereinabove with regard to FIG. 3) for further improving the path-length estimates. In some examples, as the preliminary estimate of path lengths thus obtained is substantially close to the ground truth, the preliminary estimate of path lengths may be used directly for reconstructing material basis images. That is, in some examples, the iterative optimization of the path-length estimates initialized with the preliminary estimates may be omitted from the multi-energy material decomposition. Further, in examples wherein the iterative optimization is performed, the iterative method converges to the final estimates of path lengths in fewer iterations and with increased accuracy. As the steps of performing the inverse function lookup to calculate the first estimates and generating the linear approximation of the forward model based on the first estimates are not a computational burden, the overall computational complexity of material decomposition for multiple energies is reduced. Further, according to the systems and methods provided herein, accurate material decomposition may be performed without the need to simulate or model the physics of the imaging system or the x-ray spectra for a plurality of energies and for a plurality of materials.

Figure 7:
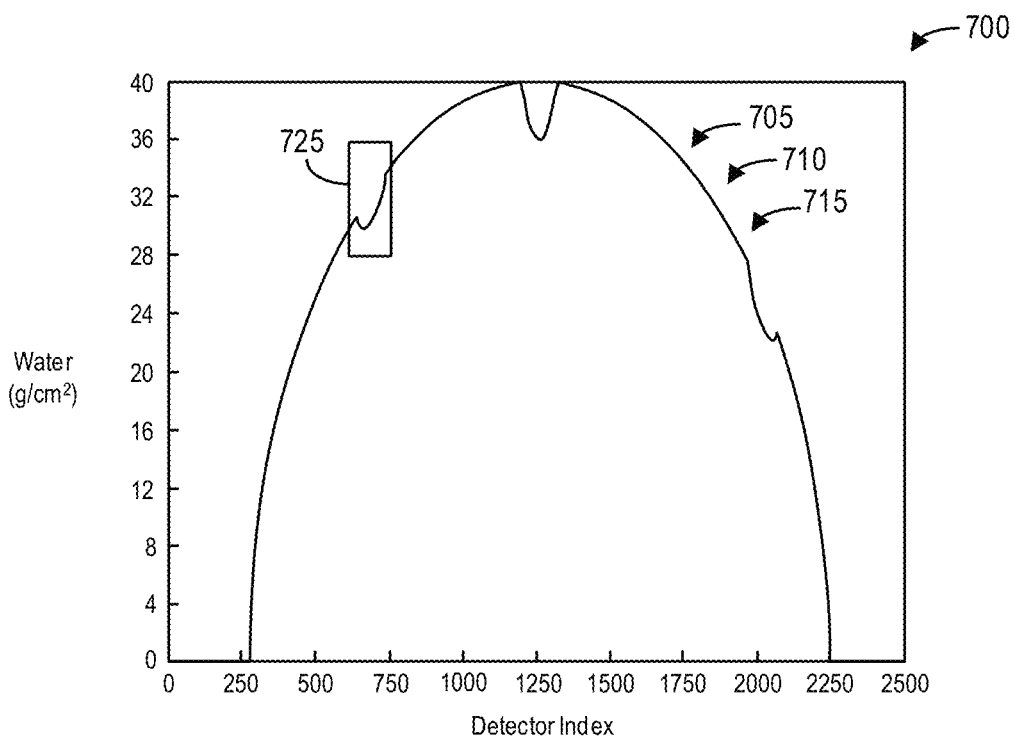
FIG. 7 shows a graph illustrating example estimated sinograms and a ground-truth sinogram for a material according to an embodiment.

To illustrate the efficacy of the techniques for multi-energy material decomposition provided herein, FIG. 7 shows a graph 700 illustrating example profiles 705 and 710 in estimated sinograms as well as the corresponding ground-truth profile 715 for a material according to an embodiment. In particular, the graph 700 depicts an example profile 705 in an estimated sinogram corresponding to the preliminary estimate (e.g., calculated according to the method 400 as described hereinabove) and an example profile 710 in an estimated sinogram corresponding to the optimized estimate (e.g., iteratively calculated at 315 as described hereinabove).

Figure 8:
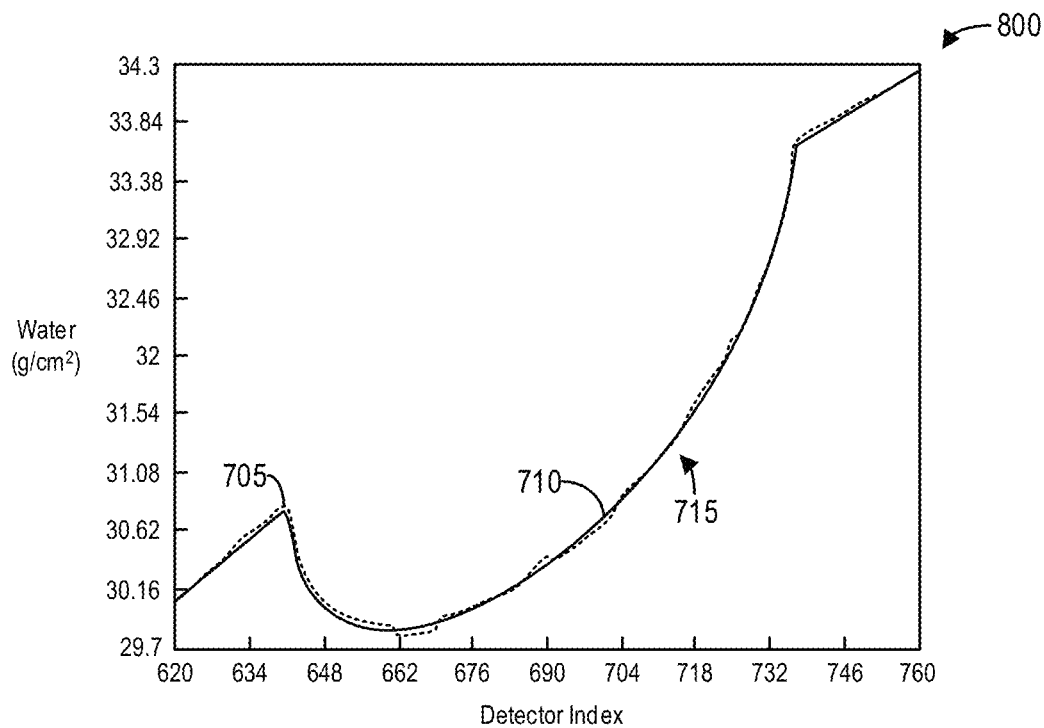
FIG. 8 shows a graph illustrating a zoomed-in view of the graph of FIG. 7.

As depicted, the example profiles 705, 710, and 715 in the estimated sinograms are similar enough to be indistinguishable in FIG. 7. To illustrate the difference between the example profiles 705, 710, and 715 in the estimated sinograms, FIG. 8 shows a graph 800 illustrating a zoomed-in view of the region 725 of the graph 700. In this view, the deviation of the preliminary estimate depicted by the example profile 705 in the estimated sinogram from the example profile 710 in the final optimized sinogram estimate is more visible. However, the final estimate depicted by the example profile 710 in the estimated sinogram is still virtually indistinguishable from the corresponding profile 715 in the ground-truth sinogram.

Figure 9:
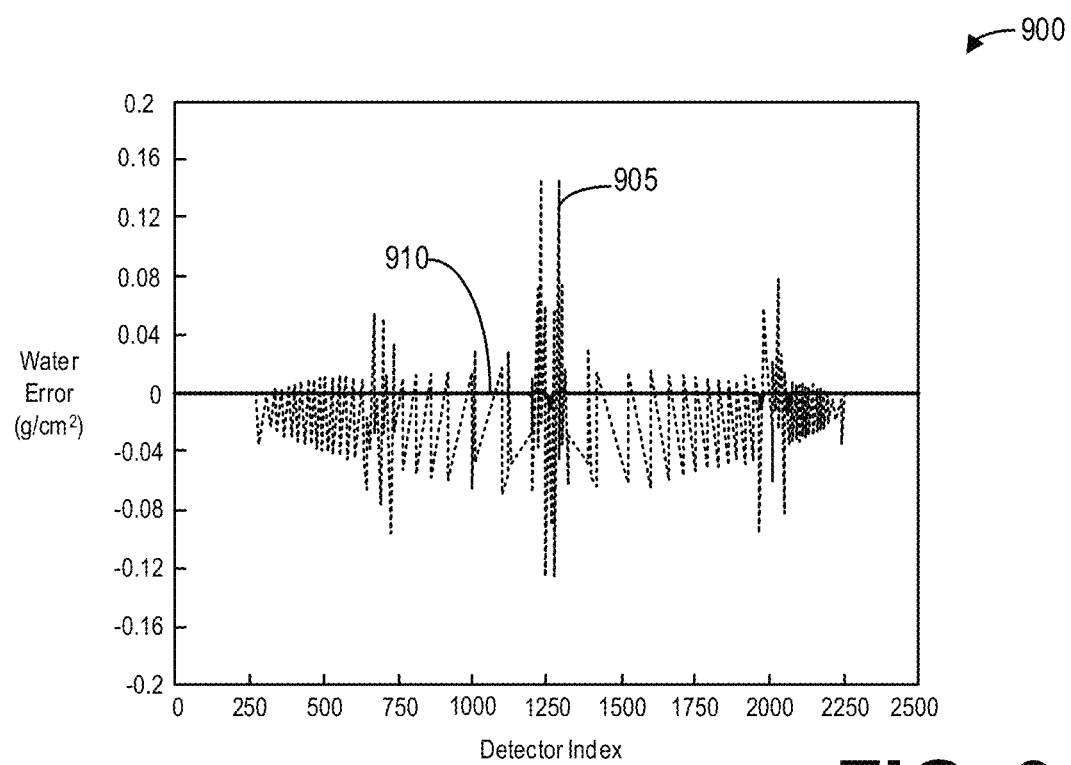
FIG. 9 shows a graph illustrating the differences of the estimated sinograms of FIG. 7 from the ground-truth sinogram according to an embodiment.
Figure 10:
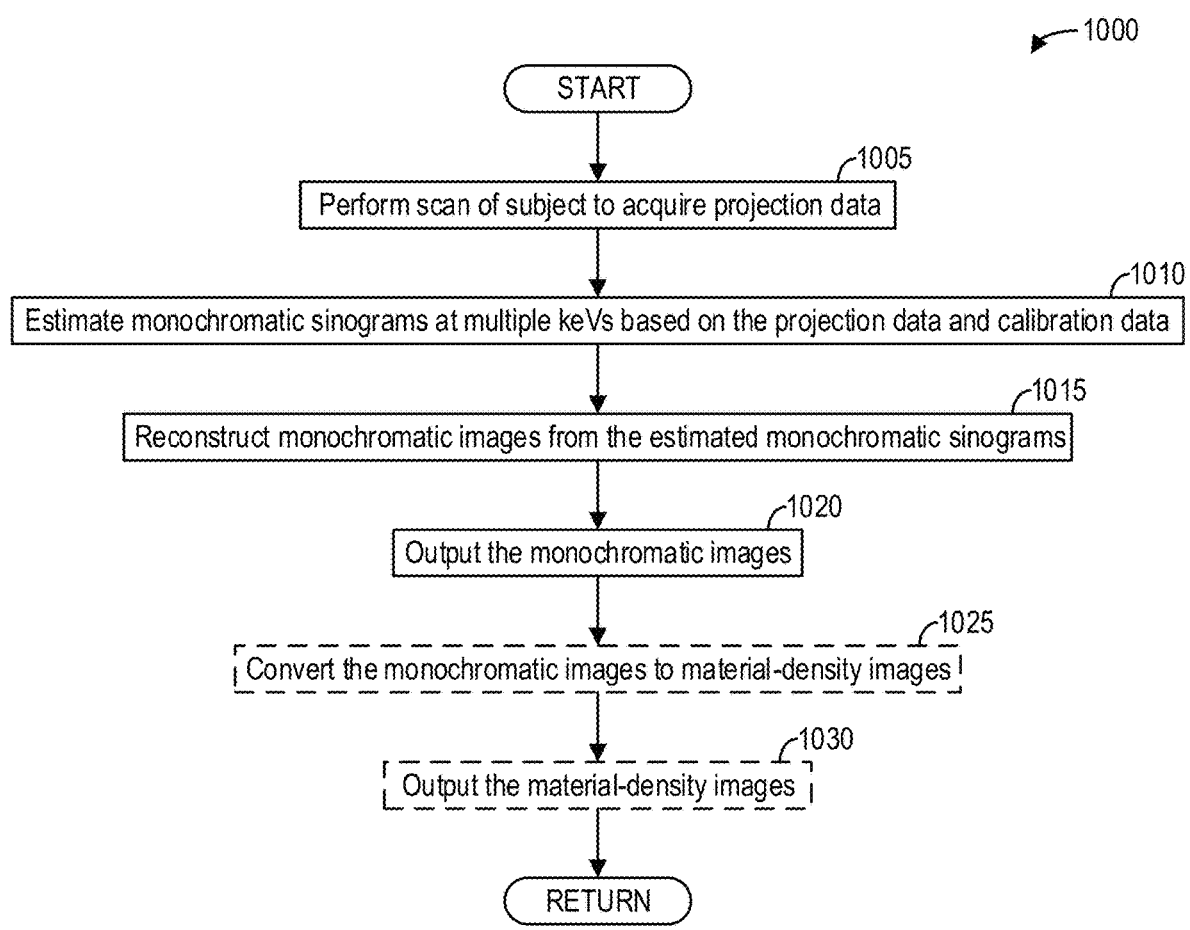
FIG. 10 shows a high-level flow chart illustrating an example method for estimating monochromatic sinograms according to an embodiment.

To quantify the difference between the example profiles 705 and 710 in the estimated sinograms from the corresponding profile 715 in the ground-truth sinogram, FIG. 9 shows a graph 900 illustrating the differences of the example profiles 705 and 710 in the estimated sinograms from the corresponding profile 715 in the ground-truth sinogram. In particular, the graph 900 depicts plots illustrating the difference 905 of the example profile 705 in the preliminary estimated sinogram from the corresponding profile 715 in the ground-truth sinogram, as well as the difference 910 of the example profile 710 in the final estimated sinogram from the corresponding profile 715 in the ground-truth sinogram. As depicted, the error or difference 905 for the preliminary estimate is greater than the error or difference 910 for the final estimate.

The difference 910 is below 0.01 $g/cm^2$ compared to the ground truth, which amounts to 0.025% error relative to the maximum integral of water density (40 $g/cm^2$ in this example), whereas the difference 905 is below 0.16 $g/cm^2$ compared to the ground truth, which amounts to 0.4% error relative to the maximum integral of water density. Thus, although the preliminary estimate is relatively effective, some image artifacts may arise from the difference 905 if material-basis images are reconstructed directly from the preliminary estimates, while using the optimized final estimates may effectively eliminate such image artifacts. Further, as the preliminary estimate is substantially close to the ground truth, using the preliminary estimate as an initial estimate for iteratively calculating path-length estimates provides a substantial improvement over using a predetermined initial estimate or an initial estimate derived from a model-based approach.

While the methods described hereinabove directly estimate the multi-material path lengths, it is possible to adapt the above methods to estimate monochromatic sinograms at multiple monochromatic energies (keVs) instead of multi-material path lengths. For example, the methods described hereinabove may be adapted to estimate monochromatic sinograms through a simple substitution of variables. As an illustrative example, FIG. 10 shows a high-level flow chart illustrating an example method 1000 for estimating monochromatic sinograms according to an embodiment. In particular, method 1000 relates to estimating monochromatic sinograms at multiple energies based on calibration data to adaptively reduce noise covariance. Method 1000 is described with regard to the systems and components of FIGS. 1 and 2, though it should be appreciated that the method 1000 may be implemented with other systems and components without departing from the scope of the present disclosure. Method 1000 may be implemented as executable instructions in non-transitory memory of the computing device 216 and/or the image reconstructor 230, for example, and may be executed by a processor of the computing device 216 and/or the image reconstructor 230 to perform the actions described herein.

Method 1000 begins at 1005. At 1005, method 1000 performs a scan of a subject to acquire projection data. The scan comprises a dual-energy CT scan or a multi-energy CT scan of the subject. To that end, method 1000 controls the x-ray controller 210 to drive the x-ray source 104 to emit x-rays at two or more energy levels, for example, while also controlling the gantry motor controller 212 and the table motor controller 226 to adjust positions of the gantry 102 and the table 114, respectively, such that the position of the x-ray source 104 relative to the subject 204 being scanned is adjusted while generating the x-rays. Method 1000 further acquires, via the DAS 214 for example, the projection data measured by energy-discriminating detectors including photon-counting detectors, such as the detector elements 202 of the detector array 108. The projection data comprises multi-energy photon-count measurements, for example, wherein the measurements of photons of different energies are sorted into predefined energy bins.

At 1010, method 1000 estimates monochromatic sinograms at multiple keVs based on the projection data and the calibration data. For example, if a vector μ of line integrals of monochromatic attenuation is expressed as:

$$\mu = [\mu_{keV1}, \ldots, \mu_{keVN}],$$

then a change of variables in the calibration data may be applied. For example, the forward model $f^{cal}$ for the calibration data may be expressed as:

$$f^{cal}(\mu) = f^{cal}(Q \times m),$$

wherein μ=Q×m represents the transformation from material path lengths m to monochromatic sinograms. Therefore, wherever the forward model $f^{cal}(m)$ is used hereinabove with regard to methods 300 and 400, the argument may be equivalently substituted such that $f^{cal}(Q^{-1} \times \mu)$. The unknown in this instance is the vector μ of monochromatic sinograms. For example, the iterative optimization may be re-expressed so that a final estimated vector $\mu^{final}$ of the monochromatic sinograms is:

$$\mu^{final} = \arg\min_{\mu} F\left[\mu, f^{cal}(Q^{-1} \times \mu), p^{meas}, I^{meas}\right],$$

subject to $\mu \in \Omega_{\mu}$, which may be solved as described hereinabove with regard to FIG. 3. Once the final estimated vector $\mu^{final}$ of monochromatic sinograms is obtained, final estimates of material path lengths $m^{final}$ may be obtained by calculating:

$$m^{final} = Q^{-1} \times \mu^{final},$$

Alternatively, the final estimates of material path lengths $m^{final}$ may be obtained through a simpler optimization of:

$$m^{final} = \arg\min_{m} \left\| m - Q^{-1} \times \mu^{final} \right\|_{W_{\mu}}^{2} + \text{prior}(m),$$

subject to $m \in \Omega_m$, wherein $W_{\mu}$ is a matrix depending on μ that weights different components of μ appropriately for statistical benefit, and prior(m) comprises a function that imposes prior information about the material path lengths m. It should be appreciated that the above expression for $m^{final}$ may be implemented in the image domain since the material decomposition process is already accomplished by calculating $\mu^{final}$ as described above, thus potentially removing any beam-hardening errors in the final estimates $\mu^{final}$ of monochromatic sinograms. For examples wherein method 1000 solves for $m^{final}$ in image space, the function prior(m) may include a variety of image-processing, machine-learning, and deep-learning-based penalty functions.

At 1015, method 1000 reconstructs monochromatic images from the estimated monochromatic sinograms. For example, method 1000 performs image reconstruction with the final estimated vector $\mu^{final}$ of monochromatic sinograms to generate respective monochromatic images at the multiple keVs. Then, at 1020, method 1000 outputs the monochromatic images. For example, method 300 may output the monochromatic images to a display device, such as the display device 232. Additionally or alternatively, method 300 may output the material-density images to mass storage 218 for storage and/or PACS 224 for remote review.

Further, in some examples, at 1020, method 1000 optionally converts the monochromatic images to material-density images. For example, method 1000 may convert the monochromatic images via direct linear transformation in the image domain to material-density images. In such examples, at 1025, method 1000 may optionally output the material-density images. For example, method 1000 may output the material-density images to a display device such as display device 232, and/or mass storage 218 for storage, and/or PACS 224 for remote review. Thus, rather than obtain material-density images and generating monochromatic images from the material-density images, the systems and methods provided herein enable the estimation of monochromatic images from projection data and calibration data, and the generation of material-density images from the monochromatic images. Method 1000 then returns.

A technical effect of the present disclosure includes the reconstruction of material basis images for a plurality of materials. Another technical effect of the present disclosure includes the reduction in computational complexity for calculating material path lengths. Another technical effect of the present disclosure includes the increased accuracy of material decomposition for two or more materials. Yet another technical effect of the disclosure includes the display of material basis images for three or more materials generated from projection data without the use of physics modeling. Another technical effect of the disclosure includes the reconstruction of two or more monochromatic images directly from projection data rather than from material basis images.

In one embodiment, a method comprises acquiring, via an imaging system, projection data for a plurality of x-ray spectra, estimating path lengths for a plurality of materials based on the projection data and calibration data for the imaging system, iteratively refining the estimated path lengths based on a linearized model derived from the calibration data, and reconstructing material-density images for each material of the plurality of materials from the iteratively-refined estimated path lengths.

In a first example of the method, estimating path lengths for the plurality of materials based on the projection data and the calibration data for the imaging system comprises estimating the path lengths for the plurality of materials based on the projection data and the calibration data without modeling physics of the imaging system, the physics of the imaging system including the plurality of x-ray spectra and a spectral response of a detector of the imaging system. In a second example of the method optionally including the first example, estimating path lengths for the plurality of materials based on the projection data and the calibration data for the imaging system comprises performing an inverse function lookup into the calibration data to generate a first estimate of path lengths for the plurality of materials that corresponds to the projection data. In a third example of the method optionally including one or more of the first and second examples, estimating path lengths for the plurality of materials based on the projection data and the calibration data for the imaging system further comprises generating a linear approximation of a forward model constructed from the calibration data, and solving a linear system of equations based on the linear approximation to obtain a preliminary estimate of path lengths for the plurality of materials. In a fourth example of the method optionally including one or more of the first through third examples, iteratively refining the estimated path lengths based on a linearized model derived from the calibration data comprises iteratively calculating a final estimate of path lengths for each material of the plurality of materials with the preliminary estimate of path lengths as an initial estimate, wherein the material-density images are reconstructed from the final estimate of path lengths for each material of the plurality of materials. In a fifth example of the method optionally including one or more of the first through fourth examples, performing the inverse function lookup into the calibration data to generate the first estimate of path lengths for the plurality of materials that corresponds to the projection data comprises selecting, for each sinogram bin, candidate vectors of material path lengths in the calibration data that when input to the forward model yield results within a threshold distance of the projection data, and calculating, for each sinogram bin, the first estimate of path lengths from a weighted summation of the candidate vectors. In a sixth example of the method optionally including one or more of the first through fifth examples, the method further comprises selecting weights for the weighted summation based on intensity measurements of the projection data, wherein a higher intensity corresponds to a higher weight. In a seventh example of the method optionally including one or more of the first through sixth examples, generating the linear approximation of the forward model comprises calculating a coefficient matrix that when multiplied by a matrix of known path lengths for each material results in a corresponding matrix of known projection measurements, wherein the calibration data comprises the known path lengths and the known projection measurements. In an eighth example of the method optionally including one or more of the first through seventh examples, solving the linear system of equations based on the linear approximation to obtain the preliminary estimate of path lengths for the plurality of materials comprises calculating a matrix of the preliminary estimate of path lengths for the plurality of materials that when multiplied by the coefficient matrix results in a corresponding matrix of projection measurements of the projection data. In a ninth example of the method optionally including one or more of the first through eighth examples, the method further comprises estimating at least two monochromatic sinograms based on the projection data and the calibration data and reconstructing at least two monochromatic images from the at least two monochromatic sinograms. In a tenth example of the method optionally including one or more of the first through ninth examples, reconstructing the material-density images for each material of the plurality of materials comprises estimating the plurality of material-density images from the at least two monochromatic images reconstructed from the at least two monochromatic sinograms using purely image-domain techniques comprising at least one of linear transformation of the at least two monochromatic sinograms and iterative schemes using image-domain prior information.

In another embodiment, a method comprises acquiring, via an imaging system, projection data for a plurality of x-ray spectra, calculating a preliminary estimate of path lengths for a plurality of materials based on the projection data and calibration data for the imaging system without modeling physics of the imaging system including the plurality of x-ray spectra and detector response to the plurality of x-ray spectra, iteratively updating the preliminary estimate of path lengths for the plurality of materials to obtain a final estimate of path lengths for the plurality of materials, and reconstructing material-density images for each material of the plurality of materials from the estimated path lengths.

In a first example of the method, calculating the preliminary estimate of path lengths for the plurality of materials comprises calculating a first estimate of path lengths based on an inverse function lookup into the calibration data, and solving a linear system of equations for the preliminary estimate of path lengths for the plurality of materials, the linear system of equations constructed based on a linear approximation of a forward model of the calibration data. In a second example of the method optionally including the first example, iteratively updating the preliminary estimate of path lengths for the plurality of materials to obtain the final estimate of path lengths for the plurality of materials comprises iteratively minimizing a statistical function with the projection data and the calibration data as inputs, initialized with the preliminary estimate of path lengths for the plurality of materials, to determine the final estimate of path lengths for the plurality of materials. In a third example of the method optionally including one or more of the first and second examples, the plurality of materials comprises at least three materials.

In yet another embodiment, a system comprises an x-ray source configured to generate a beam of x-rays towards a subject, a detector array comprising a plurality of detector elements configured to detect the beam of x-rays attenuated by the subject, and a computing device communicatively coupled to the x-ray source and the detector array, the computing device configured with instructions in non-transitory memory that when executed cause the computing device to: control the x-ray source and the detector array to scan the subject with a plurality of x-ray beams at different energy levels and acquire projection data; estimate path lengths for a plurality of materials based on the projection data and calibration data for the x-ray source and the detector array; iteratively refine the estimated path lengths based on a linearized model derived from the calibration data; and reconstruct material-density images for each material of the plurality of materials from the iteratively-refined estimated path lengths.

In a first example of the system, the computing device is further configured with instructions in the non-transitory memory that when executed cause the computing device to estimate the path lengths for the plurality of materials based on the projection data and the calibration data without modeling physics of the x-ray source and the detector array. In a second example of the system optionally including the first example, the computing device is further configured with instructions in the non-transitory memory that when executed cause the computing device to perform an inverse function lookup into the calibration data to generate a first estimate of path lengths for the plurality of materials that corresponds to the projection data, generate a linear approximation of a forward model constructed from the calibration data, and solve a linear system of equations based on the linear approximation to obtain a preliminary estimate of path lengths for the plurality of materials. In a third example of the system optionally including one or more of the first and second examples, the computing device is further configured with instructions in the non-transitory memory that when executed cause the computing device to iteratively calculate a final estimate of path lengths for each material of the plurality of materials with the preliminary estimate of path lengths as an initial estimate, wherein the estimated path lengths for reconstructing the material-density images comprise the final estimate of path lengths. In a fourth example of the system optionally including one or more of the first through third examples, the computing device is further configured with instructions in the non-transitory memory that when executed cause the computing device to estimate at least two monochromatic sinograms based on the projection data and the calibration data and reconstruct at least two monochromatic images from the at least two monochromatic sinograms. In a fifth example of the system optionally including one or more of the first through fourth examples, the system further comprises a display device communicatively coupled to the computing device, and the computing device is further configured with instructions in the non-transitory memory that when executed cause the computing device to output the material-density images to the display device for display. In a sixth example of the system optionally including one or more of the first through fifth examples, the computing device is further configured with instructions in the non-transitory memory that when executed cause the computing device to estimate the plurality of material-density images from the at least two monochromatic images reconstructed from the at least two monochromatic sinograms using purely image-domain techniques comprising at least one of linear transformation of the at least two monochromatic sinograms and iterative schemes using image-domain prior information.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
  acquiring, via an imaging system, projection data for a plurality of x-ray spectra;
  estimating path lengths for a plurality of materials based on the projection data and calibration data for the imaging system;
  iteratively refining the estimated path lengths based on a linearized model derived from the calibration data; and
  reconstructing material-density images for each material of the plurality of materials from the iteratively-refined estimated path lengths.

2. The method of claim 1, wherein estimating path lengths for the plurality of materials based on the projection data and the calibration data for the imaging system comprises estimating the path lengths for the plurality of materials based on the projection data and the calibration data without modeling physics of the imaging system, the physics of the imaging system including the plurality of x-ray spectra and a spectral response of a detector of the imaging system.

3. The method of claim 1, wherein estimating path lengths for the plurality of materials based on the projection data and the calibration data for the imaging system comprises performing an inverse function lookup into the calibration data to generate a first estimate of path lengths for the plurality of materials that corresponds to the projection data.

4. The method of claim 3, wherein estimating path lengths for the plurality of materials based on the projection data and the calibration data for the imaging system further comprises generating a linear approximation of a forward model constructed from the calibration data, and solving a linear system of equations based on the linear approximation to obtain a preliminary estimate of path lengths for the plurality of materials.

5. The method of claim 4, wherein iteratively refining the estimated path lengths based on a linearized model derived from the calibration data comprises iteratively calculating a final estimate of path lengths for each material of the plurality of materials with the preliminary estimate of path lengths as an initial estimate, wherein the material-density images are reconstructed from the final estimate of path lengths for each material of the plurality of materials.

6. The method of claim 3, wherein performing the inverse function lookup into the calibration data to generate the first estimate of path lengths for the plurality of materials that corresponds to the projection data comprises selecting, for each sinogram bin, candidate vectors of material path lengths in the calibration data that, when input to a forward model constructed from the calibration data, yield results within a threshold distance of the projection data, and calculating, for each sinogram bin, the first estimate of path lengths from a weighted summation of the candidate vectors.

7. The method of claim 6, further comprising selecting weights for the weighted summation based on intensity measurements of the projection data, wherein a higher intensity corresponds to a higher weight.

8. The method of claim 4, wherein generating the linear approximation of the forward model comprises calculating a coefficient matrix that when multiplied by a matrix of known path lengths for each material results in a corresponding matrix of known projection measurements, wherein the calibration data comprises the known path lengths and the known projection measurements.

9. The method of claim 8, wherein solving the linear system of equations based on the linear approximation to obtain the preliminary estimate of path lengths for the plurality of materials comprises calculating a matrix of the preliminary estimate of path lengths for the plurality of materials that when multiplied by the coefficient matrix results in a corresponding matrix of projection measurements of the projection data.

10. The method of claim 1, further comprising estimating at least two monochromatic sinograms based on the projection data and the calibration data and reconstructing at least two monochromatic images from the at least two monochromatic sinograms.

11. The method of claim 10, wherein reconstructing the material-density images for each material of the plurality of materials comprises estimating the plurality of material-density images from the at least two monochromatic images reconstructed from the at least two monochromatic sinograms using purely image-domain techniques comprising at least one of linear transformation of the at least two monochromatic sinograms and iterative schemes using image-domain prior information.

12. A method, comprising:
acquiring, via an imaging system, projection data for a plurality of x-ray spectra;
calculating a preliminary estimate of path lengths for a plurality of materials based on the projection data and calibration data for the imaging system without modeling physics of the imaging system including the plurality of x-ray spectra and detector response to the plurality of x-ray spectra;
iteratively updating the preliminary estimate of path lengths for the plurality of materials to obtain a final estimate of path lengths for the plurality of materials; and
reconstructing material-density images for each material of the plurality of materials from the final estimate of path lengths for the plurality of materials.

13. The method of claim 12, wherein calculating the preliminary estimate of path lengths for the plurality of materials comprises calculating a first estimate of path lengths based on an inverse function lookup into the calibration data, and solving a linear system of equations for the preliminary estimate of path lengths for the plurality of materials, the linear system of equations constructed based on a linear approximation of a forward model of the calibration data.

14. The method of claim 12, wherein iteratively updating the preliminary estimate of path lengths for the plurality of materials to obtain the final estimate of path lengths for the plurality of materials comprises iteratively minimizing a statistical function with the projection data and the calibration data as inputs, initialized with the preliminary estimate of path lengths for the plurality of materials, to determine the final estimate of path lengths for the plurality of materials.

15. A system, comprising:
an x-ray source configured to generate a beam of x-rays towards a subject;
a detector array comprising a plurality of detector elements configured to detect the beam of x-rays attenuated by the subject; and
a computing device communicatively coupled to the x-ray source and the detector array, the computing device configured with instructions in non-transitory memory that when executed cause the computing device to:
control the x-ray source and the detector array to scan the subject with a plurality of x-ray beams at different energy levels and acquire projection data;
estimate path lengths for a plurality of materials based on the projection data and calibration data for the x-ray source and the detector array;
iteratively refine the estimated path lengths based on a linearized model derived from the calibration data; and
reconstruct material-density images for each material of the plurality of materials from the iteratively-refined estimated path lengths.

16. The system of claim 15, wherein the computing device is further configured with instructions in the non-transitory memory that when executed cause the computing device to estimate the path lengths for the plurality of materials based on the projection data and the calibration data without modeling physics of the x-ray source and the detector array.

17. The system of claim 15, wherein the computing device is further configured with instructions in the non-transitory memory that when executed cause the computing device to perform an inverse function lookup into the calibration data to generate a first estimate of path lengths for the plurality of materials that corresponds to the projection data, generate a linear approximation of a forward model constructed from the calibration data, and solve a linear system of equations based on the linear approximation to obtain a preliminary estimate of path lengths for the plurality of materials.

18. The system of claim 15, wherein the computing device is further configured with instructions in the non-transitory memory that when executed cause the computing device to iteratively refine the estimated path lengths for each material of the plurality of materials with the estimated path lengths as an initial estimate.

19. The system of claim 15, wherein the computing device is further configured with instructions in the non-transitory memory that when executed cause the computing device to estimate at least two monochromatic sinograms based on the projection data and the calibration data and reconstruct at least two monochromatic images from the at least two monochromatic sinograms.

20. The system of claim 19, wherein the computing device is further configured with instructions in the non-transitory memory that when executed cause the computing device to estimate the plurality of material-density images from the at least two monochromatic images reconstructed from the at least two monochromatic sinograms using purely image-domain techniques comprising at least one of linear transformation of the at least two monochromatic sinograms and iterative schemes using image-domain prior information.

\* \* \* \* \*